United States Patent [19]

Elsheikh

[11] Patent Number: 5,877,359
[45] Date of Patent: Mar. 2, 1999

[54] UNCATALYZED LIQUID PHASE FLUORINATION OF 1230ZA

[75] Inventor: Maher Y. Elsheikh, Wayne, Pa.

[73] Assignee: Elf Atochem North America, Inc., Philadelphia, Pa.

[21] Appl. No.: 13,839

[22] Filed: Jan. 27, 1998

[51] Int. Cl.$^6$ .................................................... C07C 17/20
[52] U.S. Cl. ............................................................ 570/160
[58] Field of Search ............................................... 570/160

[56] References Cited

U.S. PATENT DOCUMENTS 5,616,819    4/1997    Boyce et al. .......................... 570/167

*Primary Examiner*—Alan Siegel
*Attorney, Agent, or Firm*—Stanley Marcus; William Mitchell

[57] ABSTRACT

An uncatalyzed liquid phase process is provided for the preparation of oligomer free 1233zd via the fluorination of 1230za with a high molar excess of HF. The 1233zd is a known intermediate useful for preparing 245fa.

1 Claim, No Drawings

UNCATALYZED LIQUID PHASE FLUORINATION OF 1230ZA

BACKGROUND OF THE INVENTION

This invention relates to preparation of an essentially oligomer free (hereinafter simply "oligomer free") 1,1,1-trifluoro-3-chloro-2-propene (1233zd) by the uncatalyzed liquid phase fluorination of 1,1,3,3-tetrachloro-2-propene (1230za), particularly to such processes wherein said 1230za is contacted with a large molar excess of hydrogen fluoride (for convenience hereafter referred to as "HF"). The 1233zd product is a known intermediate for producing 245fa, as taught, for example, in U.S. Pat. No. 5,616,819 and in copending application 08/980,747, filed Dec. 1, 1997.

U.S. Pat. No. 5,616,819 discloses that previous attempts to fluorinate 1230za to 1233zd in an uncatalyzed liquid phase reaction resulted in the formation of a substantial amount of oligomeric products (19 g of oligomeric material in Example 1.i., the result of using a 6:1 molar ratio of the HF and 1230za starting materials). It is thus an object of this invention to provide an uncatalyzed liquid phase fluorination process for successfully converting 1230za to oligomer free 1233zd.

BRIEF SUMMARY OF THE INVENTION

An uncatalyzed liquid phase process for preparing oligomer free 1233zd is provided, which process comprises (a) contacting 1230za with at least about 12 moles of HF per mole of said 1230za and (b) separating the desired oligomer free 1233zd from the resulting reaction mixture in (a). The principal by-product of this reaction is hydrogen chloride (HCl), which HCl may be removed by conventional means known in the art (such as absorption or distillation).

DETAILED DESCRIPTION

It has now been discovered that the use of high HF:1230za ratios in the uncatalyzed liquid phase fluorination of 1230za results in the formation of oligomer free 1233zd.

Preparation of the 1230za starting material is taught, for example, in U.S. Pat. No. 5,689,020.

The process of this invention may be conducted as a batch or continuous process. The HF:1230za molar ratio is typically from at least about 12:1 to about 500:1, but is preferably from about 12:1 to about 170:1. Temperatures of from about 20° C. to about 200° C. are typically used, preferably from about 50° C. to about 120° C. Pressures are typically from about 0 to about 800 psig, preferably from about 270 to about 600 psig. Residence time is normally from about 5 minutes to 24 hours, preferably from about ½ to about 5 hours. HCl, the principal by-product, may be removed from the resultant reaction mixture by methods known in the art such as by absorption (in water or caustic solution) or distillation.

The practice of the invention is illustrated in more detail in the following eight non-limiting examples. Varying mole ratios of 1230za and HF were gradually heated with stirring under the conditions, for the time, and with the results shown in the following table. HCl was removed from the resulting mixture by washing with water scrubber solution. No oligomer was detected in the resulting reaction mixture in any of the examples:

| Example # | 1 | 2 | 3 | 4 | 5 | 6 | 7 | 8 |
|---|---|---|---|---|---|---|---|---|
| Temperature (°C.) | 120 | 100 | 100 | 100 | 70 | 70 | 50 | 50 |
| Pressure (psig) | 600 | 280 | 270 | 300 | 165 | 170 | 100 | 120 |
| HF:1230za (m.r.) | 12.6 | 166 | 166 | 166 | 166 | 166 | 166 | 166 |
| Residence time (hours) | 0.5 | 1 | 3 | 5 | 1 | 3 | 1 | 3 |
| Conversion of 1230za (%) | 100 | 100 | 100 | 100 | 99 | 100 | 93 | 99 |
| Selectivity for 1233zd (%) | 97 | 93 | 95 | 97 | 92 | 97 | 71 | 85 |

I claim:

1. An uncatalyzed liquid phase process for preparing oligomer free 1,1,1-trifluoro-3-chloro-2-propene, which process comprises (a) contacting 1,1,3,3-tetrachloro-2-propene with at least about 12 moles of hydrogen fluoride per mole of said 1,1,3,3-tetrachloro-2-propene and (b) separating 1,1,1-trifluoro-3-chloro-2-propene from the resulting reaction mixture in (a).

* * * * *